United States Patent
Daniel (10) Patent No.: US 10,106,282 B2
(45) Date of Patent: Oct. 23, 2018

(54) DEVICE FOR FILLING LIQUID FOOD PRODUCTS

(71) Applicant: Hamba Filltec GmbH & Co. KG, Saarbruecken (DE)

(72) Inventor: Jan Simon Daniel, Quierschied (DE)

(73) Assignee: Hamba Filltec GmbH & Co. KG, Saarbruecken (DE)

( * ) Notice: Subject to any disclaimer, the term of this patent is extended or adjusted under 35 U.S.C. 154(b) by 0 days.

(21) Appl. No.: 15/452,578

(22) Filed: Mar. 7, 2017

(65) Prior Publication Data

US 2017/0283104 A1 Oct. 5, 2017

Related U.S. Application Data

(60) Provisional application No. 62/332,815, filed on May 6, 2016.

(30) Foreign Application Priority Data

Mar. 30, 2016 (DE) .................. 10 2016 105 780

(51) Int. Cl.
*B65B 55/04* (2006.01)
*A61L 2/24* (2006.01)
(Continued)

(52) U.S. Cl.
CPC ............... *B65B 55/04* (2013.01); *A61L 2/24* (2013.01); *B65B 1/00* (2013.01); *B65B 3/00* (2013.01);
(Continued)

(58) Field of Classification Search
CPC ... A61L 2/16; A61L 2/18; A61L 2/186; A61L 2/24; A61L 2/26; A61L 2202/23;
(Continued)

(56) References Cited

U.S. PATENT DOCUMENTS 9,782,503 B2 * 10/2017 Knott ................ A61L 2/087
2017/0049914 A1 * 2/2017 Dickner ................ B65B 3/00

FOREIGN PATENT DOCUMENTS

DE 2839543 A1 3/1980
DE 29512257 U1 10/1995
(Continued)

*Primary Examiner* — Timothy C Cleveland
(74) *Attorney, Agent, or Firm* — Von Rohrscheidt Patents (57) ABSTRACT

A device for filling liquid to pasty food products into prefabricated individual containers including a support rim, the device including carrier elements which are run by a drive continuously through the device, which carrier elements form receiving openings for the individual containers and include a top side that is oriented away from a direction of gravity and configured to carry the support rim of the individual containers that are inserted into the receiving openings; operating stations in whose operating range the carrier elements move during an endless cycle of the carrier elements in the device; at least one operating station that is configured as a sterilization device which de-germinates the carrier elements and the individual containers; a lifting device forming a portion of the sterilization device and configured to lift individual containers that are seated in the receiving openings and which contact a top side with the support rim.

8 Claims, 6 Drawing Sheets

(51) Int. Cl.
*B65B 55/10* (2006.01)
*B65B 57/08* (2006.01)
*B65B 25/00* (2006.01)
*B65B 43/59* (2006.01)
*B65B 55/24* (2006.01)
*B65B 1/00* (2006.01)
*B65B 3/00* (2006.01)
*B65B 3/04* (2006.01)
*B65B 7/28* (2006.01)
*B65B 65/02* (2006.01)
*B65D 85/72* (2006.01)

(52) U.S. Cl.
CPC .............. *B65B 3/04* (2013.01); *B65B 7/2842* (2013.01); *B65B 25/00* (2013.01); *B65B 25/001* (2013.01); *B65B 43/59* (2013.01); *B65B 55/10* (2013.01); *B65B 55/24* (2013.01); *B65B 57/08* (2013.01); *B65B 65/02* (2013.01); *B65D 85/72* (2013.01); *A61L 2202/23* (2013.01); *B65B 2210/06* (2013.01)

(58) Field of Classification Search
CPC ......... B65B 55/04; B65B 55/06; B65B 55/08; B65B 55/10; B65B 65/02; B65D 85/72
See application file for complete search history.

(56) References Cited

FOREIGN PATENT DOCUMENTS

| | | |
|---|---|---|
| DE | 10309259 A1 | 9/2004 |
| EP | 1134182 A1 | 9/2001 |
| EP | 2527260 A1 | 11/2012 |

\* cited by examiner

DEVICE FOR FILLING LIQUID FOOD PRODUCTS

RELATED APPLICATIONS

This application claims priority from and incorporates by reference German Patent Applications DE 10 2016 105 780.0 filed on Mar. 30, 2016 and U.S. Provisional Patent Application 62/133,815 filed on May 6, 2016.

FIELD OF THE INVENTION

The invention relates to a device for filling liquid to pasty food products into prefabricated individual containers which include a support rim, the device including carrier elements which are run by a drive continuously through the device, forming receiving openings for the individual containers and including a top side that is oriented away from a direction of gravity and configured to carry the support rim of the individual containers that are inserted into the receiving openings, operating stations in whose operating range the carrier elements move during an endless cycle of the carrier elements in the device, at least one operating station that is configured as sterilization device which is used for de-germinating the carrier elements and the individual containers, a lifting device forming a portion of the sterilization device with which configured to lift individual containers that are seated in the receiving openings and which contact a top side with the support rim so that a gap is formed for sterilization purposes, a control that is used at least for controlling the lifting device.

BACKGROUND OF THE INVENTION

Filling devices of this generic type are known from EP 1 134 182 A1 or EP 2 527 260 A1 also owned by the applicant. Both devices include a plurality of carrier elements which in turn include a plurality of receiving openings for individual containers. The carrier elements are run in a continuous cycle through an upper main element and a lower main element through the filling device. Thus, the carrier elements are arranged in direct contact with each other at least in a main element which includes the operating stations processing the containers. This way receiving openings are arranged in this main element in pass through direction behind each other in rows and in columns adjacent to each other transversal to the pass through direction.

The operating stations of the filling device feed individual containers, place the individual containers in receiving openings, perform sterilization of the individual containers and carrier elements, fill the individual container with food products like e.g. yogurt, a beverage or a spreadable fat material etc. Then the individual containers are covered in a sealing station with a sealing foil and closed, optionally subjected to a seal test and subsequently combined into assemblies and packaged. When easily perishable food products like e.g. yogurt are being filled a filling device is typically housed in a sterile portion. Sterile air is blown into this housing so that a positive pressure is created in this location that prevents a penetration of germs through the air.

The essential difference between both known filling and transport devices is the drive mode. In the first known device the cell plates are attached to an endless feed device, typically a chain and are transported by the chain through the device in a revolving manner. The second known device omits the endless drive device since the endless drive device can have considerable disadvantages under particular conditions.

As a matter of principle filling food products requires maintaining stringent hygiene standards wherein the hygiene standards differ from each other depending on the type of product. The instant invention relates in particular to a device for filling food products with a low acid content into individual containers like e.g. filling sauces for meals ready to eat, snacks or finger food. Products of this type are typically very sensitive so that already small germ loads which are not a problem e.g. for products with higher acid content are problematic and lead to a quick spoiling of the food products.

In order to keep the germ loading sufficiently small the sterilization device has to comply with stringent requirements since the high cyclic rate of the carrier elements only permits a small dwelling time in the sterilization device.

The carrier elements filled with the individual containers are therefore introduced into the sterilization device and covered with a fine peroxide mist. Thus, the individual containers are lifted slightly so that a gap is formed between the support rim of the container and the top side of the carrier element. The sterilizing peroxide mist penetrates through this gap also into surface portions of the carrier element that are covered otherwise.

However, there is also a need to sufficiently sterilize carrier elements without containers since cell plates without containers can run into the sterile portion of the arrangement during start up or shut down of a production cycle, during interferences in the container feed or during container sealing. This sterile portion extends from the container sterilization to the portion of container sealing.

BRIEF SUMMARY OF THE INVENTION

Thus, it is an object of the invention to provide a device of the generic type described supra, whose sterilization device also keeps cell plates without container sufficiently germ free.

The object is achieved by a device for filling liquid to pasty food products into prefabricated individual containers which include a support rim, the device including carrier elements which are run by a drive continuously through the device, which carrier elements form receiving openings for the individual containers and include a top side that is oriented away from a direction of gravity and configured to carry the support rim of the individual containers that are inserted into the receiving openings; operating stations in whose operating range the carrier elements move during an endless cycle of the carrier elements in the device; at least one operating station that is configured as sterilization device which is used for de-germinating the carrier elements and the individual containers; a lifting device forming a portion of the sterilization device which lifting device is configured to lift individual containers that are seated in the receiving openings and which contact a top side with the support rim so that a gap is formed for sterilization purposes; and a control that controls at least the lifting device, wherein the sterilization device is configured with at least one closure device which is configured to close the receiving openings of the carrier elements that do not include containers during sterilization.

It is an essential advantage of the invention that the closure device facilitates treating the container less carrier elements in the same way by the sterilization device as carrier elements whose receiving openings are occupied by individual containers. In particular the peroxide mist that is present during the rather short dwelling time of the carrier elements in the sterilization device and in the subsequent drying device behaves due to the closure element almost in an identical manner with respect to its flow and precipitation properties as it does when sterilizing carrier elements that are occupied by containers. An adjustment of the sterilization process for empty carrier elements that is possible in principle like e.g. a change of the dwelling time, an adaptation of the peroxide mist or an adaptation of the subsequent drying is not necessary due to the closure device. The device according to the invention can therefore be operated without adapting the sterilization or feed parameters also for carrier elements without containers.

Thus, it is provided that the closure element is arranged below the carrier elements to be sterilized.

Contrary to simulating inserted containers which rest on a top side of the carrier elements with a support rim of the containers the invention takes a novel approach in that it moves the closure element from below against the carrier element and thus implements the closure of the receiving openings from a bottom side of the carrier element. This has the essential advantage that the top side is fully accessible for applying the sterilization mist and the closure element does not have to penetrate into the receiving opening with a precise fit, instead the closure element can for example be applied to the bottom side of the carrier element which requires a less precise positioning of the closure element and the carrier element relative to each other than would be necessary for a simulation of an inserted container by the closure element.

It is furthermore provided that the closure element forms part of the lifting device for the individual containers.

The invention takes advantage of the technical properties of the sterilization device in that it integrates the closure element into the lifting device for the individual containers. This has many advantages. For example drives and other technical devices are provided in this portion wherein the drives and other technical devices can also be used for controlling the closure device.

It is furthermore provided that the control causes a lifting movement of the lifting device when the individual containers are inserted into the receiving openings and causes a closure movement of the closure element when the receiving openings do not include a container.

Advantageously according to this embodiment the provided drives are used for the lifting device as well as for the closure element in order to induce depending on a loading condition of the carrier element either a closure movement of the closure element or a lifting movement of the lifting device in order to lift the containers out of the carrier element receiving openings while forming a gap.

It is furthermore provided that the lifting device includes at least one lifting plate for lifting the individual containers and that the lifting plate forms the closure element.

This embodiment of the invention advantageously uses the lifting arrangement or its lifting devices itself in a double function on the one hand side the lifting device, thus a lifting plate is used for lifting the individual containers. When the carrier elements are without a container the lifting device is used as a closure device. This double function of the closure device has the essential advantage that only the control and the drive of the lifting device have to be adapted in order to achieve an effective sterilization of the carrier elements in a condition where they do not hold containers.

It if furthermore provided to use plural lifting plates and to form separately controllable functional groups in particular when the control moves the lifting plates that are combined into functional groups into a lifting position or a closing position as a function of free receiving openings or receiving openings that are loaded with containers, wherein a sterilization device that sterilizes plural carrier elements simultaneously associates at least one functional group with each carrier element that is arranged in the sterilization device.

The essential advantage is that the sterilization device is passed through by plural carrier elements and the lifting device can close through its configuration carrier elements without containers and can also lift containers in loaded carrier elements in order to perform sterilization.

BRIEF DESCRIPTION OF THE DRAWINGS

Further advantages of the invention can be derived from the subsequent description of an advantageous embodiment with reference to drawing figures, wherein.

DETAILED DESCRIPTION OF THE INVENTION

Figure 1:
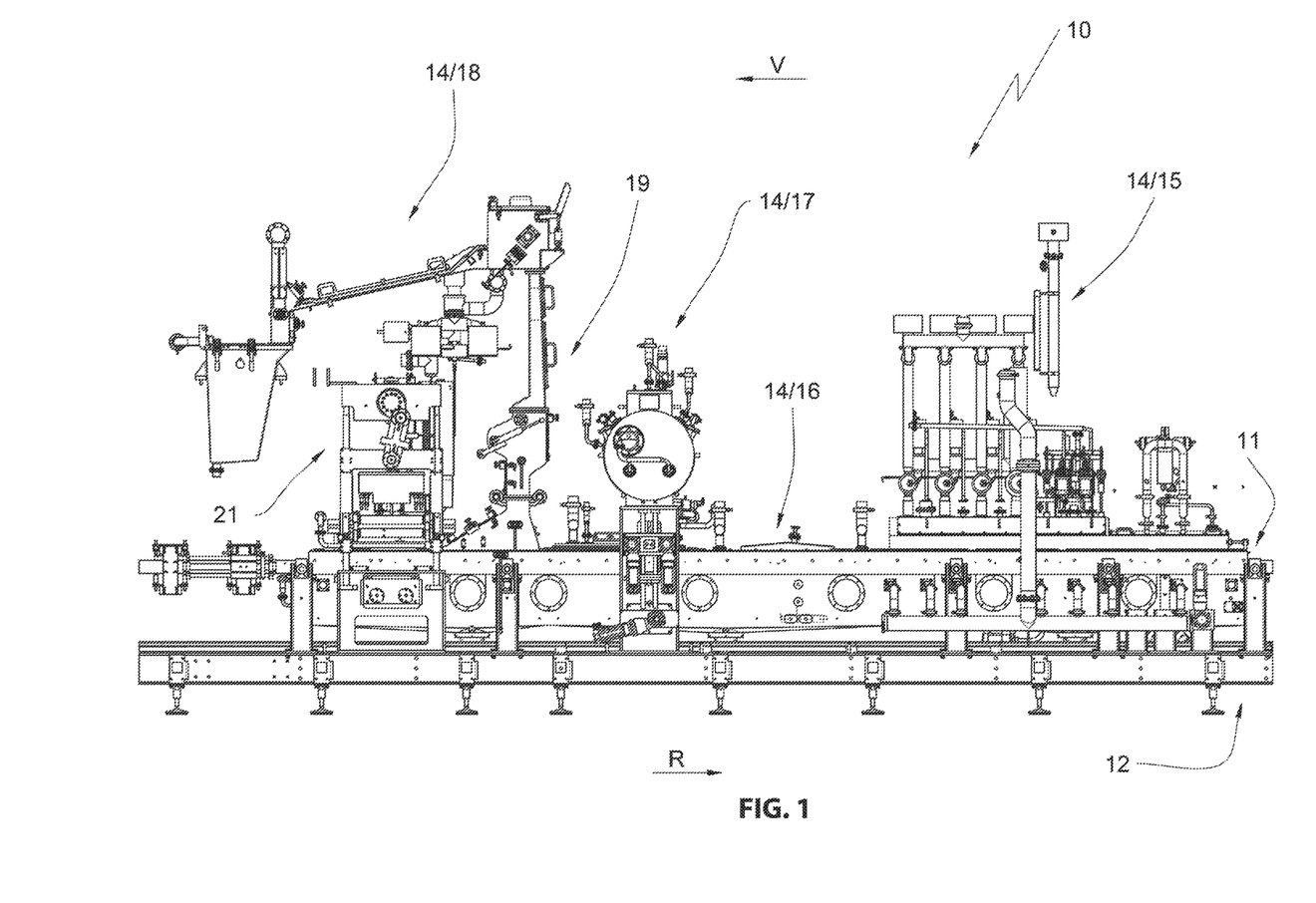
FIG. 1 illustrates a simplified representation of the device according to the invention.

The figures illustrate a device according to the invention that is designated overall with reference numeral 10 and illustrated in FIG. 1 in its entirety. The device includes an upper main element 11 and a lower main element 12 which are connected with each other by two side elements that are arranged at ends and are not illustrated. Carrier elements 13 also designated as cell plates run through the main elements 11 and 12 in a continuous cycle. For propelling the carrier elements a continuously revolving drive chain is used in the illustrated embodiment that is not visible in FIG. 1. Operating stations 14 are arranged above the upper main element 11 in a feed direction V of the upper main element 11 behind each other.

Based on the upper main element starting in FIG. 1 on a right side and terminating on a left side the following are arranged in sequence, a container insertion device 15, a sterilization device 16, a filling device 17 and a sealing device 18. The sealing device 18 is divided into a sealing foil feed 19 and the actual sealing station 21 applying the sealing foil to the individual containers 20.

A carrier element 13 coming in at a beginning of the upper main element 11 moves along the feed direction V through the upper main element 11. It is initially provided with individual containers 20 in the container insertion device 15 and then moves into the sterilization device 16 in order to sterilize the carrier element 13 and the inserted containers 20. During another feed in a direction towards the filling device 17 the carrier element 13 and the inserted individual containers are dried. Then the individual containers 20 are filled in the filling device 17 with a liquid to pasty food product, thus in particular with a mildly acidic food product 22. The unfilled head space 28 of the individual container is flushed with nitrogen in order to reduce the oxygen content to the desired amount of less than 3% and is then moved in the feed direction V to the sealing device 18. In the sealing station 21 the sealing foil is fixed by respective sealing heads above the container opening. Thereafter the containers 20 are removed from the carrier element 13 and the carrier element 13 switches at an end of the upper main element 11 through a non-illustrated side element into the lower main element 12. The carrier element 13 runs through the lower main element 12 in a return direction R until it is returned back into the upper main element 11 at an end of the lower main element 12.

Figure 1A:
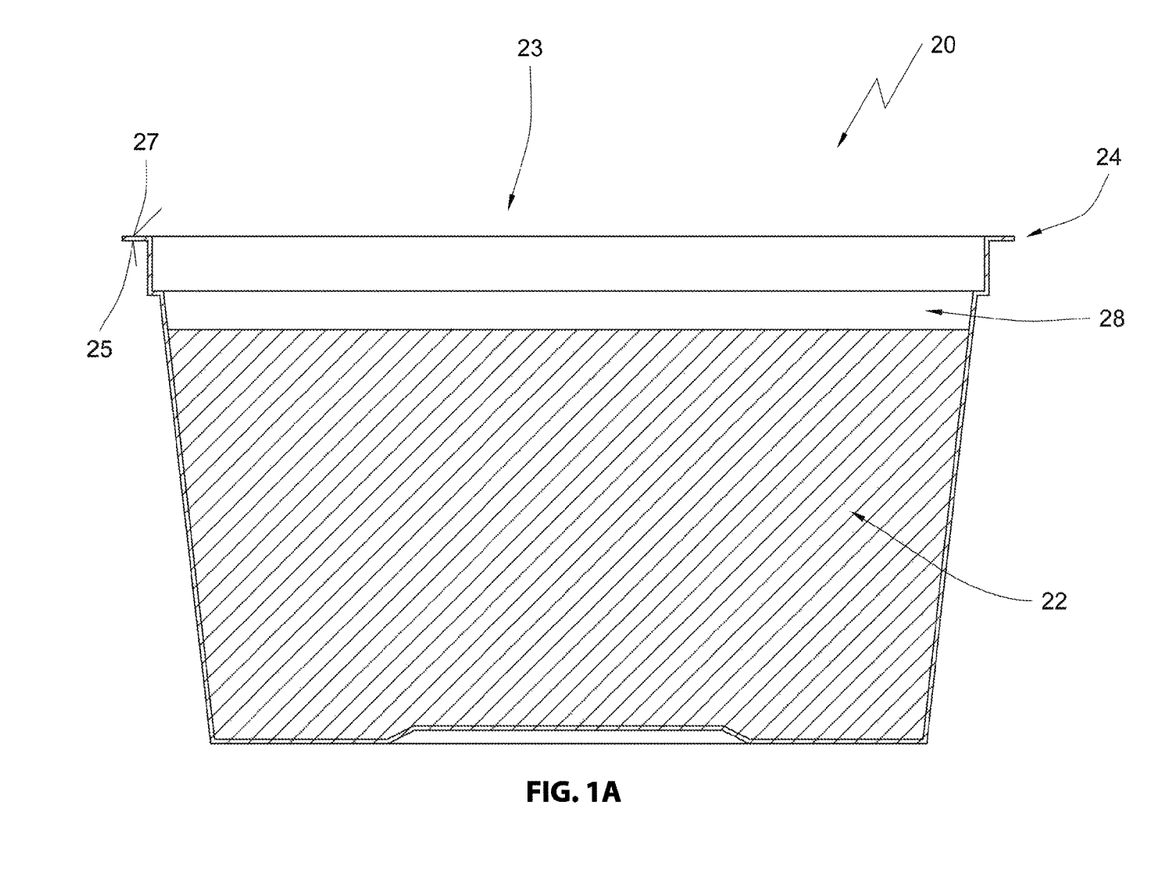
FIG. 1A illustrates a representation of an individual container.

FIG. 1A illustrates an individual container 20 in a sectional view. The container 20 is a so called individual container which is delivered prefabricated and retrieved from a stash for insertion into the carrier elements 13. The individual containers 20 inserted into the device according to the invention are thus different from deep drawn containers which are also typically used for filling with food products. The deep drawn containers, however, are formed directly before the filling process and only separated from each other after sealing the containers.

The container type that is being used causes significant differences with respect to the filling process. In deep drawn containers the carrier elements 13 are completely covered by the deep drawing foil whereas a carrier element surface is directly accessibly through intermediary spaces between the individual containers 20 when individual containers are used. Consequently when using individual containers a need for carrier element sterilization does not arise to the same extent.

The individual container 20 illustrated in FIG. 1A is filled with a food product 22 and forms a circumferential support rim 24 in a portion of the container opening 23. A bottom side 25 of the support rim serves as a contact surface on the carrier element 13 in order to prevent slippage through the receiving opening 26. The top side 27 of the support rim 24 forms a contact surface between the container 20 and a sealing foil.

Above the food product 22 and up to the support rim 24 or for a closed container 20 up to the sealing foil there is a so called head space 28 of the container 20 which is filled with a gas as a matter of principle. In particular for only slightly acidic easily perishable food products nitrogen is typically injected at this location in order to minimize oxygen content.

Figure 2:
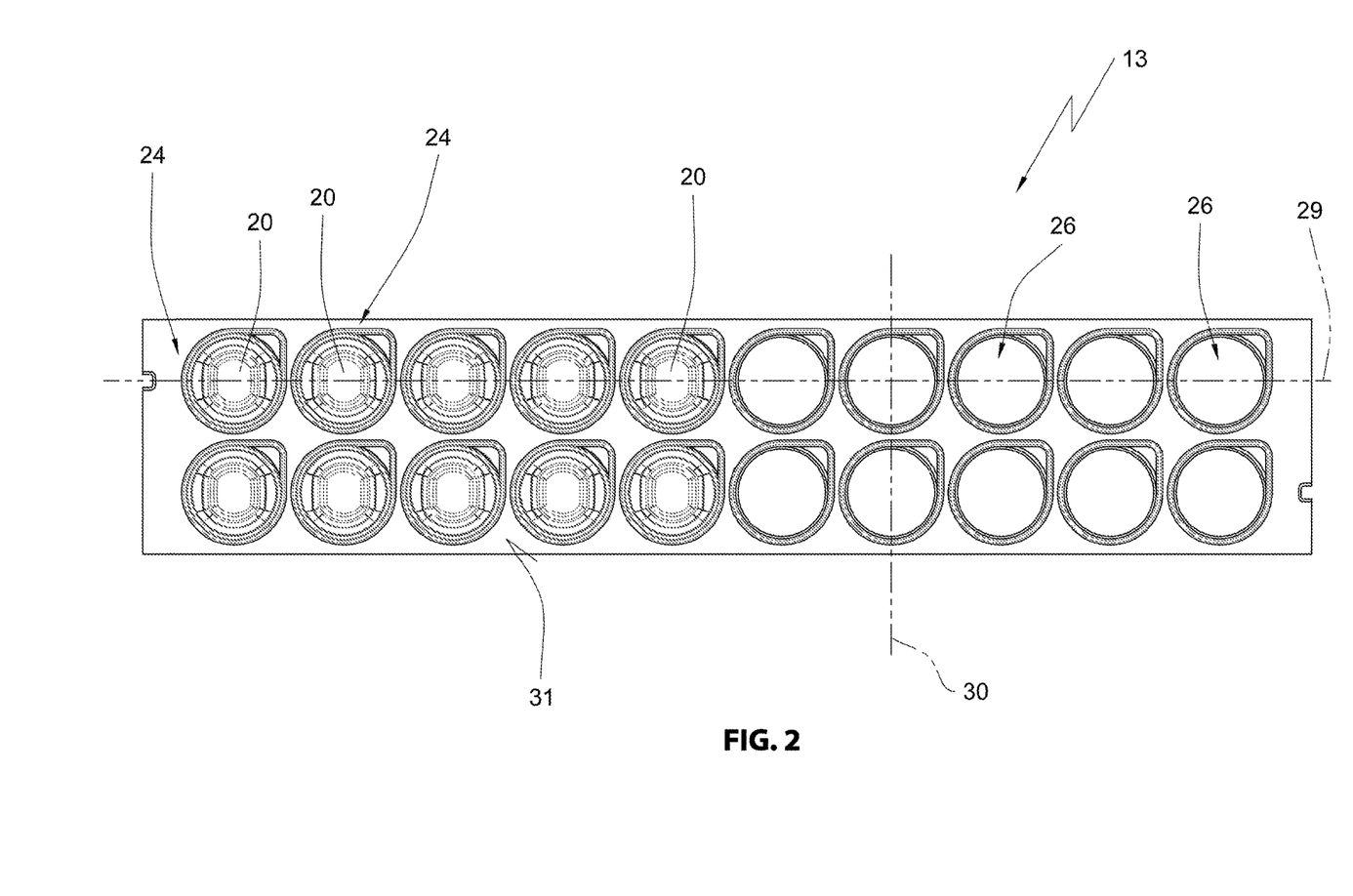
FIG. 2 illustrates a top view of a support element.

FIG. 2 illustrates a carrier element 13 which forms receiving openings 26 which are partially filled with individual containers 20 for illustration purposes. Receiving openings 26 form containers rows 29 oriented in the feed direction V and container columns 30 that are arranged adjacent to each other parallel to the feed direction. As can be derived from FIG. 2 the containers 20 are inserted into the receiving openings 26, wherein the support rim 24 of the containers contacts a top side 31 of the carrier element 13. The support rim 24 of each container 20 thus covers a surface portion of the top side 31.

Figure 3:
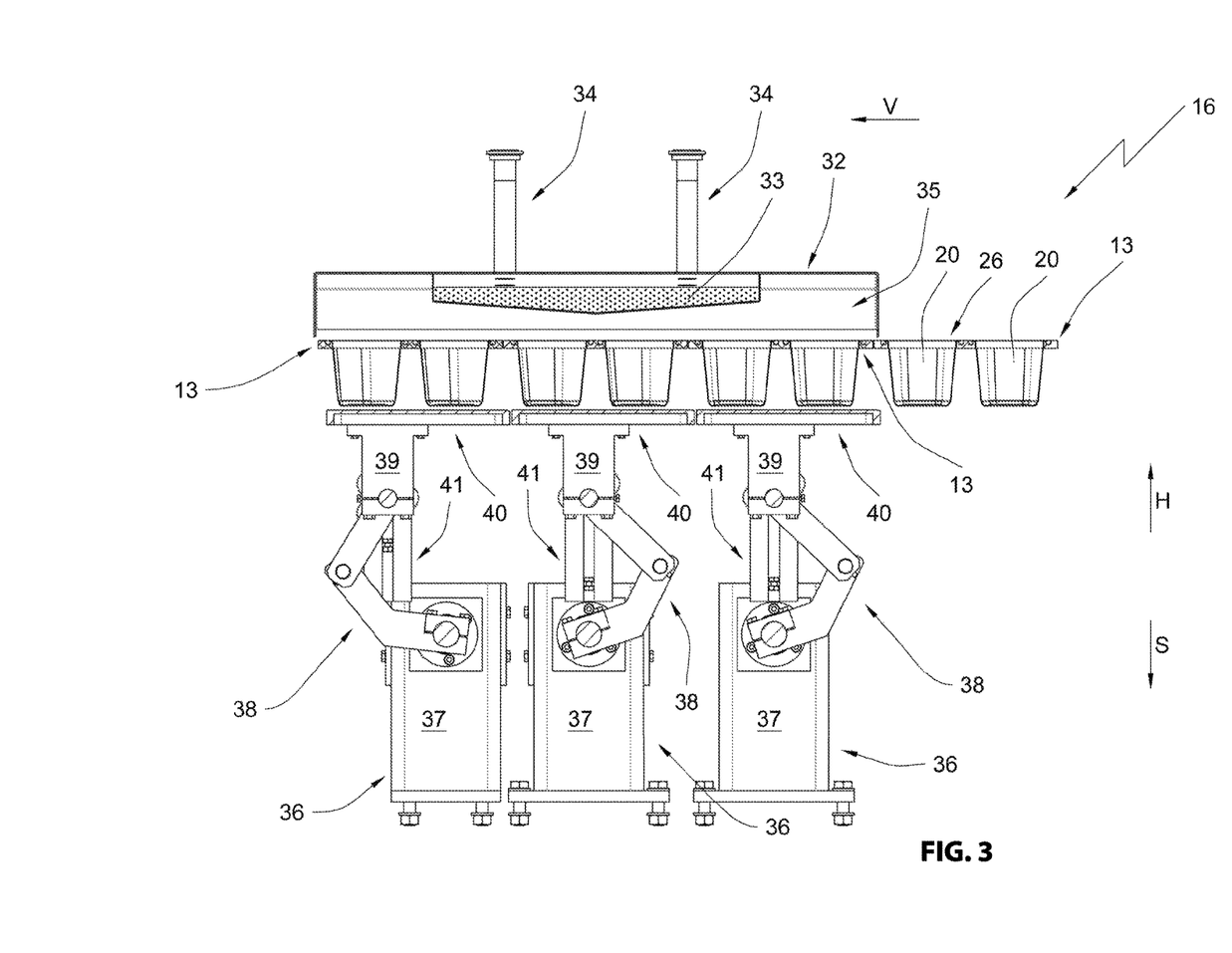
FIG. 3 illustrates a simplified representation of the sterilization device cut along the feed direction.
Figure 4:
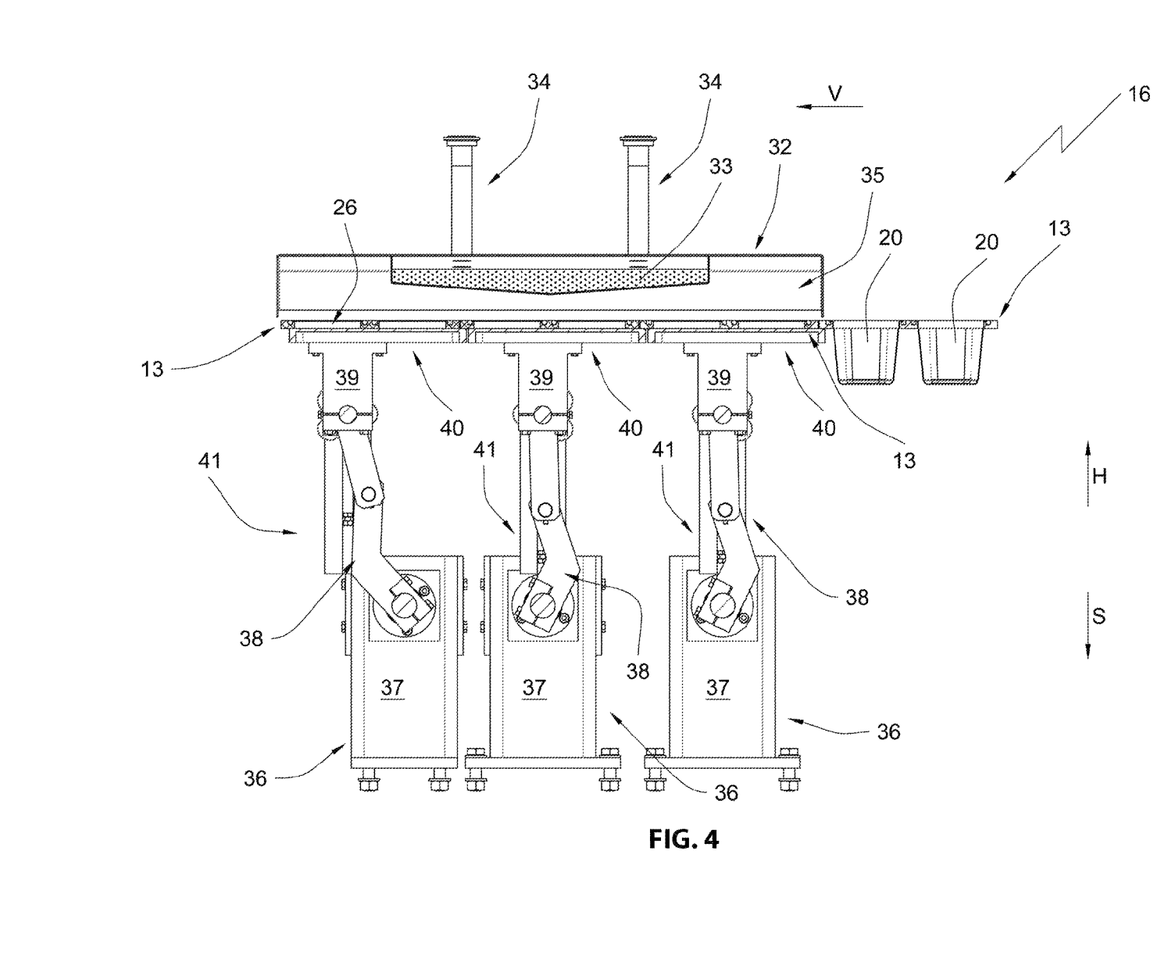
FIG. 4 illustrates a representation according to FIG. 3 with the lifting device in a closure position.
Figure 5:
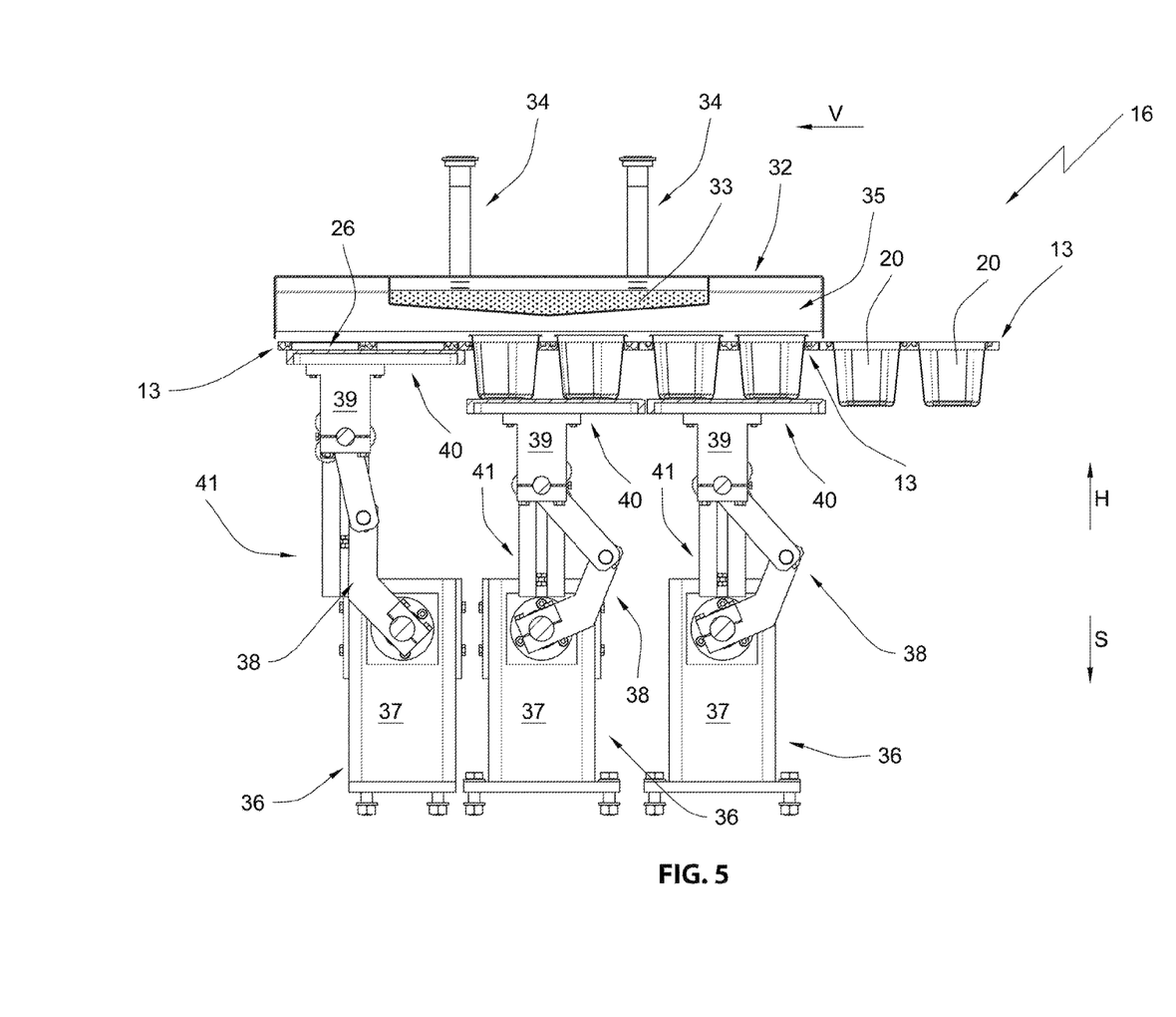
FIG. 5 illustrates a representation according to FIG. 3 with the lifting device in the closure and lifting position.

FIGS. 3-5 illustrate a schematic representation of the sterilization device 16. Only components that are relevant for the invention are illustrated. Other components were omitted in the representation for reasons of clarity.

The carrier elements 13 run through the sterilization device 16 in the feed direction V. In FIG. 3 all carrier elements 13 are configured with individual containers 20 which are inserted into the receiving openings 26.

The sterilization process is performed under a hood 32 under which a diffusor 33 is arranged which distributes a peroxide mist in the sterilization space 35 that is introduced through infeeds 34. Three lifting devices 36 are arranged below the carrier elements 13 in a portion of the sterilization hood 32. Thus, each of the lifting devices 36 is arranged below exactly one carrier element 13 and initially includes a drive unit 37. The drive unit 37 actuates an actuation arm 38 which is used for lifting or lowering a plunger 39. The plunger 39 includes a lifting plate 40 on a side oriented towards the carrier element 13. Each plunger 39 is supported in a rail 41 which provides a vertical lift movement H and a vertical lowering movement S.

In FIG. 3 the lifting plates 40 are in a lowered position which facilitates feeding the cell plates 13 forward. FIG. 3 also illustrates normal operations of the sterilization device 16. During normal operations each carrier element 13 below the hood 32 is covered with individual containers 20. Before letting the peroxide mist into the sterilization space 35 the lifting plates 40 go through a lift movement in the direction H. The lift movement brings the lift plates 40 in contact with the base of the individual containers 20, wherein a continued lift movement lifts the containers 20 out of the carrier element 13. The lifting process generates a gap between the support rim 24 of each container 20 and the top side 31 of each carrier element 13. The peroxide mist that is blown in does not only wet the inner surfaces of the containers and free surface portions of the carrier elements 13 but also reaches the gap provided between the support rim 24 and the top side 31 so that the carrier elements 13 are also sterilized in portions arranged below the support rim 24. After sterilization the lifting plates are moved back into their starting position by a lowering movement S which puts the containers 20 back into the carrier elements 13 again. Thereafter a feed cycle is performed which typically moves the carrier element that is in front in the feed direction to the next operating station. The next sterilization process of the device 10 starts when the lifting plates 40 are raised again.

FIG. 4 illustrates the sterilization device 16 according to the representation in FIG. 3 but the carrier elements that are arranged below the sterilization hood 32 are without containers. The situation illustrated in FIG. 4 can occur for example when the device 10 starts up when carrier elements 13 that are not yet provided with containers 20 run through the device 10. Through suitable sensors a control operating the lifting device 16 detects that the support elements 13 are provided with containers 20 and moves the lifting plates 40 beyond their lifting position into a closure position closing the receiving openings 26 because the carrier elements are not provided with containers. In this closure position the lifting plates 40 contact the bottom side of the carrier elements 13 and thus close the receiving openings 26. The blown in peroxide mist can spread in the sterilization space 35 without negative interference from unoccupied receiving openings 26 and can wet the carrier element surfaces. Before the next feed cycle the lifting plates 40 are moved back into their lowered position which then provides a free feed movement of the carrier elements 13.

A different operating situation of the sterilization device 16 is illustrated in FIG. 5. One of the carrier elements 13 arranged below the sterilization hood 32 is kept without a container. Two other carrier elements 13 are configured with individual containers 20. It is illustrated herein how the receiving openings 26 of the carrier element 13 without container are closed by the lifting plate 40. For this purpose the control of the lifting device 16 has forced a closure movement in a direction H upon the drive 37 that is arranged in front in the feed direction V. In the other two drives merely a lifting movement was caused so that the containers 20 inserted into the carrier elements 13 are raised for the subsequent sterilization process so that a gap is formed. After the sterilization process is completed the lifting plates 40 are lowered into their starting position. Also in this operating situation in order to facilitate a feeding of the carrier elements 13 in the feed direction V.

It can be derived in particular from the representation according to FIG. 5 that the individual lifting devices 36 can be controlled individually so that an individual reaction can be executed in response to a respective loading situation of the carrier elements 13 with containers 20. Thus, the lifting devices 36 are separately controllable functional groups in the instant embodiment.

An advantageous sterilization device 16 with a lifting device 36 for a device 10 for filling food products was shown which provides a safe sterilization process for carrier elements 13 without containers. Thus, the lifting device 36 is used to control the closure devices which close the receiving openings 26 of the carrier elements 13 from below. Particularly advantageously the lifting devices 40 that are provided anyhow are used as a closure device. In a sterilization device 16 which sterilizes plural carrier elements 13 simultaneously it is provided to use plural lifting devices 36, wherein a lifting device 36 is associated with each carrier element 13. The separate control of the lifting devices 36 facilitates running the filling device as a function of the carrier elements 13 being loaded with containers 20 or not.

REFERENCE NUMERALS AND DESIGNATIONS

10 device
11 upper main element
12 lower main element
13 carrier element/cell plate
14 operating station
15 container insertion device
16 sterilization device
17 filling device
18 sealing device
19 sealing foil feed
20 individual container/individual cup
21 sealing station
22 food product
23 container opening
24 support rim
25 bottom side of 24
26 receiving opening
27 top side of 24
28 head space of 20
29 row
30 column
31 top side of 13
32 hood
33 diffusor
34 feed
35 sterilization space
36 lifting device
37 drive unit
38 actuation arm
39 plunger
40 lifting plate
41 rail H lifting movement
S lowering movement
R return direction
V feed direction

What is claimed is:

1. A device for sterilizing prefabricated individual food product containers including a respective support rim, the device comprising:
    carrier elements which are run by a drive through the device continuously, which carrier elements form receiving openings for the individual containers and include a top side that is oriented away from a direction of gravity and configured to carry the support rim of the individual containers that are inserted into the receiving openings;
    operating stations in whose operating range the carrier elements move during an endless cycle of the carrier elements in the device;
    at least one operating station that is configured as a sterilization device which sterilizes the carrier elements and the individual containers;
    a lifting device forming a portion of the sterilization device and configured to lift the individual containers that are seated in the receiving openings and which contact the top side with the respective support rim so that a gap is formed between the respective support rim and the carrier elements facilitating sterilization of the individual containers and the carrier elements; and
    a control that controls at least the lifting device,
    wherein the sterilization device is configured with at least one closure device which is configured to close the receiving openings of the carrier elements that do not include the individual containers during sterilization.

2. The device according to claim 1, wherein the closure element is arranged below the carrier elements to be sterilized.

3. The device according to claim 1, wherein the closure element is part of the lifting device for the individual containers.

4. The device according to claim 2, wherein the control causes a lift movement of the lifting device when the individual containers are arranged in the receiving openings and causes a closure movement of the closure device when the receiving openings are not provided with the individual containers.

5. The device according to claim 3, wherein the lifting device includes at least one lifting plate for lifting the individual containers and that the lifting plate forms the closure element.

6. The device according to claim 5, wherein plural lifting plates are provided and form separately controllable functional groups.

7. The device according to claim 6, wherein the control moves the lifting plates combined in a functional group into a lifting position or a closure position as a function of the receiving openings being vacant or provided with the individual containers.

8. The device according to claim 7, wherein the sterilization device sterilizes plural carrier elements simultaneously so that each functional group arranged in the sterilization device is associated with at least one carrier element.

* * * * *